United States Patent [19]

Bulteau et al.

[11] 4,077,976

[45] Mar. 7, 1978

[54] ENAMINES, THEIR DERIVATIVES AND PROCESSES OF PRODUCTION

[75] Inventors: Gerard Bulteau, Paris; Jacques Acher, Itteville; Jean-Claude Monier, Lardy, all of France

[73] Assignee: Societe d'Etudes Scientifiques et Industrielles de l'Ile-de-France, Paris, France

[21] Appl. No.: 694,877

[22] Filed: Jun. 11, 1976

[30] Foreign Application Priority Data

Jun. 12, 1975 France .................................. 75 18344

[51] Int. Cl.$^2$ ............................................ C07D 207/08
[52] U.S. Cl. ........................... 260/326.2; 260/239 BF; 260/239 B; 260/293.85; 260/293.87; 260/326.43; 260/326.46; 260/326.5 L; 260/326.84; 424/274; 424/267; 424/244

[58] Field of Search ......................... 260/326.2, 326.43

[56] References Cited

U.S. PATENT DOCUMENTS 3,878,223  4/1975  Garmaise et al. ................. 260/326.2

OTHER PUBLICATIONS

Burger, Medicinal Chemistry, 2nd ed., p. 497 (1960).
Burger, Medicinal Chemistry, 3rd ed., p. 1588 (1970).

Primary Examiner—Donald G. Daus
Assistant Examiner—Mary Vaughn
Attorney, Agent, or Firm—Frank M. Nolan

[57] ABSTRACT

The enamines of this invention are useful in the preparation of certain benzamides employed in the treatment of emesis in mammals.

2 Claims, No Drawings

ENAMINES, THEIR DERIVATIVES AND PROCESSES OF PRODUCTION

The application relates to enamines and derivatives thereof.

The enamines of this invention may be employed in the production of benzamides useful in the treatment of emesis in mammals such as the benzamides described in Miller et al. U.S. Pat. No. 3,342,826.

The enamines of this invention have the following formula:

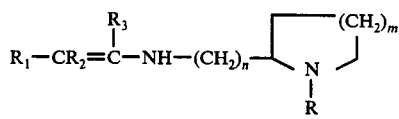

in which:

R may be a $C_{1-5}$ alkyl group or $C_{2-5}$ alkenyl group, containing or not containing a reactive function such as alcohol, thioalcohol, ketone, thioketone, ether or thioether, $R_1$ may be an alkyl group with 1 to 5 carbon atoms, or an alkyl carboxylate group, or an acyl group, $R_2$ may be hydrogen or an alkyl group with 1 to 5 carbon atoms, $R_3$ may be an alkyl group with 1 to 5 carbon atoms, or an alkyl carboxylate group, $R_2$ and $R_3$ may be joined together via a methylene group, and $n$ and $m$ may have the values 1, 2, 3, as well as their dextrorotary and levorotary isomers, their acid addition salts, their quaternary ammonium salts, and a process for their preparation.

The compounds of the invention may be used for example to synthetise substances having valuable therapeutic properties, i.e. antiemetic benzamides.

The compounds of the invention may be prepared by reacting ketones having a mobile hydrogen atom in the α-position, aliphatic β-diketones, or β-ketone esters with an amine of the following general formula:

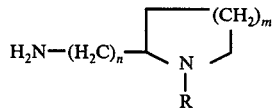

in which: $n$, $m$ and R have the previously given meanings.

The example given hereinafter to illustrate the invention is not limiting:

Methyl N-(1-ethyl-2-pyyrrolidylmethyl)-3-aminocrotonate hydrochloride.

38.4 g (0.3 mole) of N-ethyl-2-aminomethylpyrrolidine and a drop of hydrochloric acid $d = 1.18$ were added into a 250 ml flask provided with a stirrer, a thermometer, a condenser and a dropping funnel; 38.4 g (0.3 mole) of methyl acetoacetate were added drop by drop. The temperature reached 54° C by the end of the introduction. The mixture was next allowed to return to ambient temperature while stirring, and 150 ml of methylene chloride and 5 g of magnesium sulphate were then added. The mixture was stirred for one hour, filtered, the solvent was evaporated in vacuo, and the residue was distilled. 55 g of methyl N-(1-ethyl-2-pyrrolidylmethyl)-3-aminocrotonate were obtained. (Yield: 81.1%; boiling point - 3 mm/Hg: 132°–134° C).

55 g (0.24 mole) of methyl N-(1-ethyl-2-pyrrolidylmethyl)-3-aminocrotonate, 250 ml of acetone and sufficient amount of ethanolic hydrochloric acid to bring the pH to 1 were added into a 500 ml beaker, while stirring the mixture. The product was allowed to crystallise out and was then filtered and dried in an oven at 50° C.

60.8 g of methyl N-(1-ethyl-2-pyrrolidylmethyl)-3-aminocrotonate hydrochloride were obtained. (Yield: 95.2%; m.p. 140° C).

What is claimed is:

1. Enamines and their non-toxic acid addition salts, said enamines having the formula:

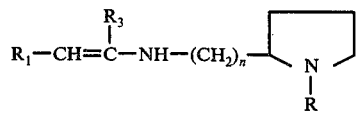

in which R is a $C_{1-5}$ alkyl group having or not having a hydroxy or carbonyl group, $R_1$ is a methyl carboxylate group, $R_3$ is an alkyl group with 1 to 5 carbon atoms, and $n$ is 1, 2, or 3.

2. Methyl N-(1-ethyl-2-pyrrolidylmethyl)-3-aminocrotonate hydrochloride.

* * * * *

UNITED STATES PATENT OFFICE
CERTIFICATE OF CORRECTION

Patent No. 4,077,976　　　　　　　　　　Dated March 7, 1978

Inventor(s) Gerard Bulteau et al.

It is certified that error appears in the above-identified patent and that said Letters Patent are hereby corrected as shown below:

Column 2, line 12, "38.4" should read --- 34.8 ---.

Signed and Sealed this

Twentieth Day of June 1978

[SEAL]

Attest:

RUTH C. MASON
Attesting Officer

DONALD W. BANNER
Commissioner of Patents and Trademarks